United States Patent [19]

Zimmerman et al.

[11] Patent Number: 5,169,772
[45] Date of Patent: Dec. 8, 1992

[54] LARGE SCALE METHOD FOR PURIFICATION OF HIGH PURITY HEPARINASE FROM FLAVOBACTERIUM HEPARINUM

[75] Inventors: Joseph J. Zimmerman, Boston; Charles L. Cooney, Brookline, both of Mass.

[73] Assignee: Massachusetts Institute of Technology, Cambridge, Mass.

[21] Appl. No.: 726,646

[22] Filed: Jul. 2, 1991

Related U.S. Application Data

[63] Continuation of Ser. No. 203,235, Jun. 6, 1988, abandoned.

[51] Int. Cl.$^5$ .............................................. C12N 9/88
[52] U.S. Cl. .................... 435/232; 435/850; 435/252.1
[58] Field of Search ...................... 435/232, 252.1, 850

[56] References Cited

U.S. PATENT DOCUMENTS

| | | | |
|---|---|---|---|
| 4,341,869 | 7/1982 | Langer, Jr. et al. | 435/232 |
| 4,373,023 | 2/1983 | Langer et al. | 435/2 |

FOREIGN PATENT DOCUMENTS 54-107584  8/1979  Japan.

OTHER PUBLICATIONS

Silva, et al., *Biochem. and Biophys. Research Communications*, 56(4), 965-972 (1974).
Linhardt, et al., *Int. J. Biochem*, 17(11), 1179-1183, (1985).
Ototani, et al., *Carbohydrate Research*, 88, 291-303 (1981).
Yang, et al., *The Journal of Biological Chemistry*, 260(3), 1849-1857 (Feb. 10, 1985).
Hovingh, et al., *The Journal of Biological Chemistry*, 245(22), 6170-6175 (Nov. 25, 1970).
Bernstein, et al., *Methods in Enzymol.*, 137, 515-529 (1988).
Stecher et al., *The Merck Index*, Eighth Ed., p. 879, 1968.
Yang, et al., *Thrombosis Research* 44, 599-610 (1986).
Langer, et al., *Science* 217, 261-263 (1982).
Charm et al., "Scale-Up of Protein Isolation", in *Methods in Enzymology*, vol. XXII (New York, Academic Press, 1971), pp. 476-490.
Linker et al., "Heparinase and Heparitinase from Flavobacteria", in *Methods in Enzymology*, vol. XXVII (N.Y. Academic Press, 1972), pp. 902-911.
Galliher et al., "Heparinase Production by Flavobacterium", *Appl. Environ. Microbiol.*, vol. 41, No. 2, pp. 360-365, 1981; (CA 94:154929n).
Yang et al., "Purification and Characterization of Heparinase from Flavobacterium Heparinum", J. Biol. Chem., vol. 260, No. 3, pp. 1849-1857, 1985.
Nakamura et al., "Purification and Properties of Bacteroides Heparinolyticus Heparinase (Heparin Lyase, EC 4.2.2.7)", J. Clin. Microbiol., vol. 26, No. 5, pp. 1070-1071, May 1988.

*Primary Examiner*—Douglas W. Robinson
*Assistant Examiner*—Marian C. Knode
*Attorney, Agent, or Firm*—Kilpatrick & Cody

[57] ABSTRACT

The present invention is an improved process for purification of active heparinase and heparinase like enzymes from Gram negative organisms, in particular, *Flavobacterium heparinum*. The primary advantage of the process is the fact that it allows large scale processing and high yield of heparinase. The heparinase is released from the periplasmic space of the organism by osmotic shock treatment, first into an osmotically stabilized medium, secondly into a non-stabilized medium having a pH of approximately pH 6.0 and 8.6 with subsequent release into a second non-stabilized medium containing approximately 0.15 M sodium chloride, followed by fractionation by cation exchange chromatography, and, optionally, electrophoresis or gel filtration chromatography. Two proteins having heparinase activity have been isolated, one having a molecular weight of approximately 42,000 Daltons and the other having a molecular weight of 65,000 to 75,000 Daltons.

Also described is the construction of a library for screening for the genes encoding the proteins having heparinase activity and two assay for detecting organisms producing heparinase, either *F. heparinum* or genetically engineered organisms.

13 Claims, 1 Drawing Sheet

LARGE SCALE METHOD FOR PURIFICATION OF HIGH PURITY HEPARINASE FROM FLAVOBACTERIUM HEPARINUM

The U.S. government has rights in this invention by virtue of National Institute of Health grant number GM25810.

This is a continuation of copending application Ser. No. 07/203,235 filed on Jun. 6, 1988, now abandoned.

BACKGROUND OF THE INVENTION

This invention is a method for the purification of heparinase and other eliminases from F. heparinum.

Heparinase is an eliminase which cleaves heparin at alphaglycosidic linkages in heparin's major repeating unit: ->4)-2-deoxy-2-sulfamino- -D-glucopyranose 6-sulfate-(1->4)-alpha-L-idopyranosyluronic acid 2-sulfate-(1->. Heparin is used clinically, both in vitro and in vivo, to inhibit blood coagulation. A mucopolysacchride with a wide range of molecular weights of up to 20,000, average molecular weight 13,500, heparin works by directly inhibiting thrombin and activated Factor X as well as other serine esterases in the blood.

The anticoagulant effect of heparin is neutralized clinically either by precipitation with protamine or as described in U.S. Ser. No. 044,245 entitled "Extracorporeal Reactors Containing Immobilized Species" filed May 22, 1987 by Howard Bernstein, et al., and U.S. Ser. No. 044,340 entitled "Bioreactor Containing Suspended, Immobilized Species" filed Jun. 6, 1987, by Lisa E. Freed, et al., reactors containing immobilized heparinase. The heparinase is immobilized to prevent leaching of the heparinase into the body via the blood passing through the reactor.

Sulfatase free heparinase, also designated catalytic grade heparinase, is required to completely remove the anticoagulant properties of heparin by enzymatic degradation. As described in U.S. Pat. No. 4,341,869 to Langer, et al., heparinase is produced by bacteria such as Flavobacterium heparinum. The organism is grown, the cells lysed, debris removed by centrifugation, and the cell extract passed through a hydroxylapatite, $3Ca_3(PO_4)_2$ or $Ca(OH)_2$ or $Ca_{10}(PO_4)_6(OH)_2$ column. A hydroxylapatite column can provide 10 to 100 fold enzyme enrichment when the protein is eluted from the column at high salt concentrations in a step-wise fashion. As described, higher yield of the enzyme is obtained by step-wise elution of the heparinase using a phosphate buffer solution of increasing sodium chloride concentration, ranging from 0.01M sodium phosphate pH 6.8 up to 0.10M sodium phosphate 0.19M sodium chloride pH 6.8.

This purification process was greatly improved by combining the hydroxylapatite chromatography with repeated gel filtration chromatography and chromatofocusing, as described by Yang, et al. in "Purification and Characterization of Heparinase from Flavobacterium heparinum" J.Biol.Chem. 260(3), 1849-1857 (1985).

The purified heparinase, a protein, has a molecular weight of 42,900±1000 Daltons with a pI value of 8.5.

Although these methods are useful in preparing laboratory reagent quantities and characterizing the enzyme, they are inadequate for preparing heparinase in the quantity and the purity required for large scale clinical application. Additionally, the purification scheme outlined would be difficult to adapt to large scale recovery of the enzyme.

Other methods which have been used to extract proteins from the periplasmic space of Gram negative bacteria include osmotic shock treatment as the initial step. Typically these procedures include an initial disruption in osmotically stabilizing medium followed by selective release in non-stabilizing medium. The composition of these media (pH, protective agent) and the disruption methods used (chloroform, lysozyme, EDTA, sonication) vary among specific procedures reported. None of these has as yet been successfully applied to the purification of catalytic grade heparinase.

It is therefore an object of the present invention to provide a method for preparing highly pure heparinase in large quantities for use in commercial and clinical applications.

It is another object of the present invention to provide a method for isolation of other eliminases from F. heparinum.

It is a still further object of the invention to provide large quantities of purified, enzymatically active heparinase and other eliminases.

SUMMARY OF THE INVENTION

F. heparinum cells, concentrated by ultrafiltration, are subjected to an osmotic shock treatment to release active heparinase from the periplasmic space. In the preferred embodiment, disruption of the cell envelope is induced by exposing the cells to an osmotically stabilized medium (20% sucrose), with or without EDTA, followed by an initial release of periplasmic material into a non-stabilized medium (10 mM phosphate, at a pH between 6.0 and 8.6) with the subsequent release of heparinase and other eliminase activity into a second non-stabilized medium (10 mM phosphate, 150 mM sodium chloride, at a pH between 6.0 and 8.6). This three step process allows an initial five to ten-fold purification with a yield of up to 75% activity. In particular, the impurities proving most difficult to remove by previously reported procedures are removed during the first two steps of the osmotic shock treatment.

Following the removal of sodium ions by diafiltration, the concentrated material is fractionated by cation exchange chromatography, preferably using a FPLC Mono S column. Heparinase activity is present in two proteins, one approximately 42,000-43,000 Dalton protein and one 65,000-75,000 protein. Overall yield is typically 25% with a 200-300 fold increase in purity.

The effectiveness of the osmotic shock treatment may be improved by varying the pH and ionic strength of the two release media. Furthermore, a scale-up of this process may be carried out by employing mass flow ion exchange devices.

A method for construction of a gene library and methods of screening for organisms producing heparinase are also described.

DETAILED DESCRIPTION OF THE INVENTION

Figure 1:
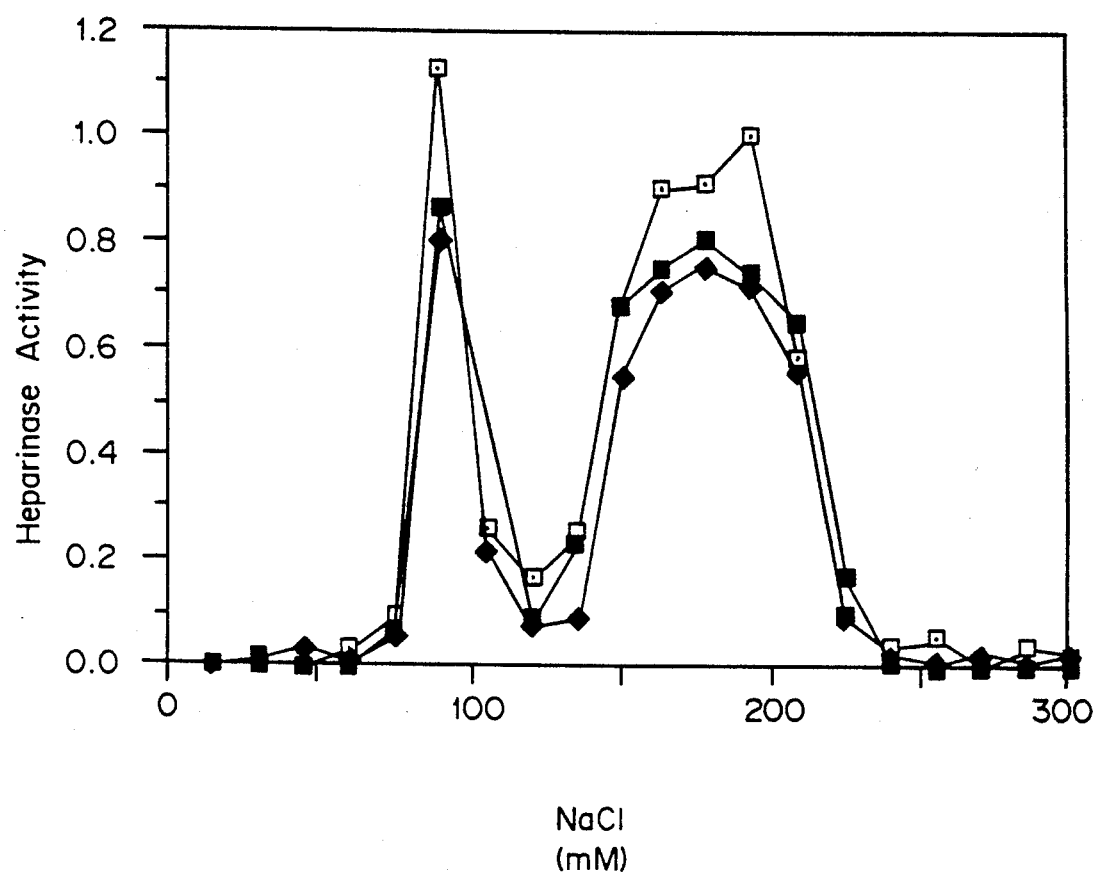
FIG. 1 is an activity chromatogram of the material released by the three step osmotic shock procedure fractionated by cation exchange chromatography using a FPLC Mono S column eluted with a gradient of 0 to 0.3 M NaCl (one ml fractions were collected during the elution gradient and assayed for heparinase activity using Azure A dye).

The preferred method of the present invention for large scale heparinase purification from bacteria is to produce heparinase in a fermentation reactor containing an organism such as *Flavobacterium heparinum* or any other Gram negative organism which has been engineered or mutated to produce heparinase, to remove the culture medium and concentrate the cells by a method such as ultrafiltration or centrifugation, to subject the concentrated cells to a three-step osmotic shock, to separate out the cells and non-specific periplasmic material, to concentrate the remaining periplasmic material by diafiltration using a membrane having a 10,000 molecular weight cutoff to remove water and salts, to separate out the heparinase by ion exchange chromatography of the concentrated solution containing 10 mM NaCl solution (preferably on a cation exchange fast protein liquid chromatography column), and to further purify the material eluted from the column having heparinase activity by gel electrophoresis or gel filtration.

SELECTIVE PERIPLASMIC PROTEIN RELEASE

*F. heparinum* cells obtained from Alfred Linker, Veterans Administration Hospital, Salt Lake City, Utah, were grown at 30° C. in 2.8 L shaker flasks containing 500 ml defined medium (3 g $K_2HPO_4$/L, 1.5 g $KH_2PO_4$-$H_2O$/L, 0.5 g NaCl/L, 1.0 g $NH_4Cl$/L, 2 mM $MgSO_4$-$7H_2O$, 0.2 g L-histidine/L, 0.2 g L-methionine/L, 8 g glucose/L, 1 g heparin/L, and $10^{-4}$ mM each of $NaMoO_4$-$2H_2O$, $CoCl_2$-$6H_2O$, $MnSO_4$-$H_2O$, $CuSO_4$-$5H_2O$, $FeSO_4$-$7H_2O$ and $CaCl_2$). The organism can be stored for up to two weeks on agar plates containing 1% Difco agar in defined medium, containing 4 g heparin/L as the sole carbon source or indefinitely in 10% DMSO at $-80°$ C.

Heparinase activity is assayed by observing the metachromatic shift of azure A from blue to red in the presence of heparin according to the procedure of Galliher, et al., *Appl. Environ. Microbiol.* 41,360-365 (1981). The change in absorbance is measured at 620 nm in the linear range of the assay and compared with a standard curve of 0 to 8 mg/ml heparin in assay buffer (0.25M Na Acetate, 0.0025M Ca Acetate, pH 7.0). One unit of activity by this assay corresponds to the amount of enzyme which degrades 1 mg of heparin/h.

Beta galactosidase activity is measured by the method of Miller, Experiments in Molecular Genetics, Cold Spring Harbor Laboratory, Cold Spring Harbor, N.Y. Protein concentrations are measured by the Bio-Rad protein assay. Growth of the organism is monitored by measuring the absorbance of cell suspensions 600 mn. Viable cell counts are determined by plating appropriate dilutions on defined medium agar plates.

The osmotic shock procedure is as follows. Cells are first suspended in an osmotically stabilizing medium, for example, a protective medium containing 20% sucrose, 10 mM sodium phosphate, pH 7.0. Following this treatment, the cells are resuspended consecutively into two non-stabilizing (recovery) media: 1) 10 mM sodium phosphate, pH 7.0 (a low ionic strength buffered solution) and 2) 10 mM sodium phosphate containing 150 mM sodium chloride, pH 7.0 (a buffered salt solution). The cells are initially harvested and subsequently removed from each solution by centrifugation at 7000 g, 10 min, in a Sorval RC-2B refrigerated centrifuge. Unless otherwise stated, all procedures are carried out at pH 7.0 and 4° C. at cell concentration of $5 \times 10^{10}$ cells/ml. An aliquot of cells, not subjected to osmotic shock, is sonicated with a Branson W-350 sonifier, 15 min, 50% pulsed, #6) and used as a 100% control. Supernatants from the osmotic release solutions and the sonicated cells are dialyzed in 10 mM phosphate, 150 mM NaCl prior to evaluation for enzymatic activity and protein content.

As shown in Table 1, the higher specific activity of the released enzyme as compared to the specific activity of the whole cell (sonicate control) indicates that heparinase is preferentially released into the non-stabilizing media. Maximal release of heparinase is achieved when disrupted cells are first washed with the low salt solution follwed by a wash in high salt solution. Furthermore, only a small quantity of betagalactosidase activity is detected in the release supernatants indicating that cytoplasmic material is not released to any great extent by this procedure. EDTA, SDS, lysozyme, toluene or chloroform can be added to the non-stabilizing medium to aid in disruption of the cell and release of the enzyme from the periplasmic space or the cells can be subjected to freezing and thawing. Sonication will also selectively release the periplasmic proteins but is not readily controllable. None of these latter additives nor sonication are more effective than sucrose alone, however.

TABLE 1

Specific release of heparinase from *F. heparinum* by three step osmotic shock treatment.

| SAMPLE[a] | HEPARINASE | | | β-GALACTOSIDASE | | PROTEIN | |
|---|---|---|---|---|---|---|---|
| | Activity (U/ml) | % | Sp. act. | Activity (U/ml) | % | Total (mg/ml) | % |
| SONICATE | 29.22 | 100.0 | 29.2 | 1.50 | 100.0 | 1.00 | 100.0 |
| SUCROSE | 0.00 | 0.0 | 0.0 | 0.02 | 1.3 | 0.02 | 2.0 |
| LOW SALT | 1.31 | 4.5 | 26.2 | 0.01 | 0.7 | 0.05 | 5.0 |
| HIGH SALT | 11.63 | 39.8 | 83.2 | 0.01 | 0.7 | 0.14 | 14.0 |

[a]all samples contained $5 \times 10^{10}$ cells/ml

Table 2 demonstrates the dependence of the enzymatic release on the ionic strength of the recovery solutions. Osmotically stabilized cells were divided into two equal batches and resuspended separately in low and high salt solutions. After the initial treatment, the cells were divided again into two batches and resuspended separately in the two non-stabilizing solutions. All supernatants were collected and assayed for heparinase activity and protein content. The results show the importance of using all three solutions: 20% sucrose, low salt, and high salt, in that order.

TABLE 2

Dependence of enzymatic release on the ionic strength of recovery solutions.

| SAMPLE | HEPARINASE | | | PROTEIN | |
|---|---|---|---|---|---|
| | Activity (U/ml) | % | Sp. act. | Total (mg/ml) | % |
| SONICATE | 50.74 | 100.0 | 26.0 | 1.95 | 100.0 |
| I: low salt | 6.47 | 12.8 | 38.1 | 0.17 | 8.7 |
| II: low salt | 4.58 | 9.0 | 65.4 | 0.07 | 3.6 |
| high salt | 21.66 | 42.7 | 216.6 | 0.10 | 5.1 |

TABLE 2-continued

Dependence of enzymatic release on the ionic strength of recovery solutions.

| SAMPLE | | HEPARINASE | | PROTEIN | |
|---|---|---|---|---|---|
| | Activity (U/ml) | % | Sp. act. | Total (mg/ml) | % |
| I: high salt | 0.72 | 1.4 | 24.0 | 0.03 | 1.5 |
| II: low salt | 1.52 | 3.0 | 76.0 | 0.02 | 1.0 |
| high salt | 2.33 | 4.6 | 233.0 | 0.01 | 0.5 |

Table 3 demonstrates the effects of EDTA and pH on the
release of heparinase from *F. heparinum* using the three step osmotic shock process. The presence or amount of EDTA does not seem to alter the release of the heparinase. However, the amount of heparinase released to the low salt solution increases with increasing pH over pH 6.0 to pH 8.7. The greatest overall recovery for either low salt or high salt fractions is at pH 7.5.

TABLE 3

Effects of EDTA and pH on the release of heparinase from *F. heparinum* by three step osmotic shock.

| SAMPLE | EDTA[a] (mM) | pH[b] | HEPARINASE Activity (U/ml) | % |
|---|---|---|---|---|
| Effect of EDTA: | | | | |
| SONICATE | | 7.0 | 22.6 | 100.0 |
| low salt | 0.0 | 7.0 | 4.03 | 17.8 |
| high salt | | | 10.25 | 45.2 |
| low salt | 1.0 | 7.0 | 3.59 | 15.8 |
| high salt | | | 10.87 | 48.0 |
| low salt | 2.0 | 7.0 | 2.26 | 10.0 |
| high salt | | | 10.50 | 46.3 |
| low salt | 5.0 | 7.0 | 2.57 | 11.3 |
| high salt | | | 11.80 | 52.1 |
| low salt | 10.0 | 7.0 | 3.51 | 15.5 |
| high salt | | | 10.80 | 47.7 |
| low salt | 20.0 | 7.0 | 5.61 | 24.8 |
| high salt | | | 11.07 | 48.9 |
| Effect of pH: | | | | |
| SONICATE | | 7.0 | 24.44 | 100.0 |
| low salt | 0.0 | 6.0 | 1.29 | 5.3 |
| high salt | | | 5.07 | 20.7 |
| low salt | 0.0 | 6.7 | 3.35 | 13.7 |
| high salt | | | 10.95 | 44.8 |
| low salt | 0.0 | 7.5 | 4.29 | 17.6 |
| high salt | | | 19.75 | 80.8 |
| low salt | 0.0 | 8.6 | 6.18 | 25.3 |
| high salt | | | 16.76 | 68.6 |

[a] amount of EDTA added in the first stage
[b] pH of recovery solutions

The stage of cell growth has an effect on the extent of recovery. The maximal recovery occurs from samples taken during mid to late exponential phase, at the maximal growth rate of $0.21^{-1}$ for *F. heparinum*. The specific activity of heparinase released increases throughout exponential growth while the total amount of protein released remains relatively constant. The decrease in recovery of heparinase during stationary growth phase appears to be related to a decrease in the amount of protein released rather than a decline in specific activity.

In general, the amount of protein released into each of the recovery solutions is approximately equal, 5-8% of the total cell protein. At pH 7.0, heparinase is preferentially released to the high salt solution which contains 65-80% of the total released activity.

Using these methods, the conditions for optimum recovery of heparinase using a three step osmotic shock treatment can be determined. Based on the data in Tables 1, 2, and 3, an improved initial purification step was designed in which heparinase is selectively released from *F. heparinum* and simultaneously separated from other periplasmic components by varying the salt concentration in release media.

While the protein content in each recovery solution is approximately equal, 5 to 8% of total cell protein, approximately 75% of the heparinase activity released is found in the high salt recovery fraction with a typical ten-fold increase in specific activity. Exposing osmotically stabilized cells immediately to a high salt solution results in a poor release of protein. Additionally, replacing the third step of the procedure with a low salt solution wash fails to release heparinase activity comparable to that released into a high salt solution.

ION EXCHANGE CHROMATROGRAPHY AND ELECTROPHORESIS

Heparinase, isolated from *F. heparinum* by osmotic release, can be further purified by cation exchange chromatography, preferably using a fast protein liquid chromatography (FPLC) apparatus (Mono S, Pharmacia Fine Chemicals, Piscataway, N.J.). Samples are dialyzed and loaded in a 10 mM phosphate buffer at pH 7.0, and eluted with a linear salt gradient ranging from 0.0 to 0.3M NaCl at a flow rate of 1 ml/min.

More than 70% of the total protein applied is not absorbed to the column. Activity is recovered in two fractions containing less than one percent of the total protein, as shown in FIG. 1. The protein eluting at 150 mM NaCl has a molecular weight of 42,900 Daltons. The specific activity of this fraction is in the range of 2000-3000 U/mg protein. A second enzyme is eluted at 75 mM NaCl. The heparinase activity of the material eluting at 75 mM NaCl appears to be sensitive to freezing, however, greater than 90% activity is retained for as long as seven days in 10 mM phosphate, 0.1M NaCl, pH 7.0, ±20% glycerol, at −20° C.

Enzyme preparations can be further purified and analyzed by gel filtration on a molecular sieve such as Sephadex G100 or SDS-PAGE using the procedure of Laemmli, Nature 227,680-685 (1970)(12.5% acrylamide resolving gels). The 42,900 Dalton protein contains three other major contaminants are removed by electrophoresis. The material eluting at 75 mM NaCl can be further purified by chromatography using a FPLC apparatus with a gel filtration matrix such as Superose 12, Pharmacia Fine Chemicals, Piscataway, N.J. The sample is loaded directly from the cation exchange chromatography and eluted with 10 mM sodium phosphate, 0.1M NaCl, pH 7.0 at a flow rate of 0.1 ml/min. Heparinase activity is detected in the fraction having a molecular weight in the range of 65,000 to 75,000 Daltons. When analyzed by SDS-PAGE, the material having the greatest activity has a molecular weight of 70,000, even under reducing conditions.

LARGE SCALE PRODUCTION BY FERMENTATION

Following the two major purification steps, osmotic release and FPLC, two concentration steps, ultrafiltration and diafiltration, are used to facilitate the handling of larger amounts of material, the results of which are shown in Table 4 for a ten liter fermentation of *F. heparinum* grown to 2 g/L DCW and concentrated by microfiltration using a 0.1µ Romicon hollow fiber membrane device to one liter. Material released to the high salt solution was concentrated by diafiltration using a 10,000 Dalton cutoff ultrafiltration membrane and fractionated by FPLC cation exchange chromatography. Typically, 20-25% of the heparinase activity is recovered with a 200 to 300 fold increase in specific activity.

TABLE 4

Recovery of heparinase from a 10 liter fermentation of *F. heparinum*.

| STEP | Total activity (units) | Recovery of activity (%) | Sp. act. (U/mg) | Total protein (mg) |
| --- | --- | --- | --- | --- |
| FERMENTATION | 13350 | 100 | 4.6 | 2930 |
| ULTRAFILTRATION | 12700 | 95 | ND | ND |
| OSMOTIC SHOCK | 7000 | 52 | 27.4 | 255 |
| DIAFILTRATION | 6750 | 51 | ND | ND |
| FPLC | 3200 | 24 | 2100 | 1.5 |

PRODUCTION OF ANTIBODIES AND HYBRIDIZATION PROBES FOR CLONING

The purified heparinase proteins obtained by gel electrophoresis or gel filtration can be used to produce antibody using methods known to those skilled in the art. For example, antibodies can be generated by injection of a protein in a suitable adjuvant such as Freund's incomplete adjuvant into an animal like a rabbit or goat. Alternatively, monoclonal antibodies can be prepared by immunizing a mouse and fusing the spleen cells with hybridoma cells following elicitation of the antibody.

The material eluted from the SDS-PAGE was of sufficient purity to allow sequencing using methods and equipment available to those skilled in the art. The results in Table 5 show a similar composition profile for both proteins although some discrepancies are evident, most notably glutamine/glutamate, lysine and methionine. The sequence for the 42,000 Dalton protein is modified at the N-terminus, as determined by inhibition of the Edmund degradation technique. The nucleotide and amino acid sequences can be used in the preparation of hybridization probes and other means for obtaining nucleic acid sequences encoding heparinase, for subsequent use in genetically engineering organisms for increased production of heparinase or production under external control.

TABLE 5

Amino acid composition of proteins from *F. heparinum* displaying heparinase activity.

| | 42,000 D protein | | 70,000 D protein | |
| --- | --- | --- | --- | --- |
| amino acid | mole % | residues/ 400 | mole % | residues/ 720 |
| glutamine/glutamate | 14.6 | 58 | 10.3 | 77 |
| asparagine/aspartate | 17.3 | 69 | 14.6 | 106 |
| serine | 7.6 | 30 | 5.3 | 38 |
| glycine | 6.9 | 28 | 7.1 | 51 |
| histidine | 1.6 | 6 | 2.2 | 16 |
| arginine | 3.0 | 12 | 3.7 | 27 |
| threonine | 6.4 | 26 | 5.8 | 42 |
| alanine | 11.9 | 48 | 10.1 | 73 |
| proline | 3.0 | 12 | 4.8 | 35 |
| tyrosine | 3.4 | 14 | 3.6 | 26 |
| valine | 5.3 | 21 | 5.2 | 38 |
| methionine | 1.0 | 4 | 2.1 | 15 |
| isoleucine | 3.5 | 14 | 3.6 | 99 |
| leucine | 4.4 | 18 | 6.5 | 47 |
| phenylalanine | 2.9 | 12 | 2.9 | 21 |
| lysine | 7.4 | 30 | 12.1 | 88 |

METHODS FOR SCREENING OF EXPRESSION LIBRARY FOR HEPARINASE GENES

Assays were developed for screening large populations of genetically engineered organisms for heparinase production. Previous attempts to screen using antibodies to heparinase have been unsuccessful due to extensive cross reactivity with several other *F. heparinum* proteins. The assays and methods for screening can be used to isolate and characterize the gene for either the 42,000 Dalton heparinase or the 65,000-75,000 Dalton protein with heparinase activity.

An agar plate assay was developed based on the precipitation of heparin from human blood by electrostatic association with protamine sulfate. Heparinase assay plates consisting of 0.25M sodium acetate, 0.0025M $CaCl_2$, 1.0 g heparin from porcine intestinal mucosa (Hepar Industries, Franklin, OH)/liter, and 1.5% agarose (BRL), pH 7.0 are prepared. Plates are innoculated with the cells to be screened for heparinase production. As a control, heparinase is isolated by the method described above and applied in various quantities, 0.0, 0.01, 0.10, and 1.00 U, in 10 μl of 10 mM sodium phosphate, 150 mM NaCl, pH 7.0 to a plate which is then incubated at 37° C. for 1 h. A 2% protamine sulfate (salmon, Sigma Chemical Co, St. Louis, Mo.) solution is poured over the surface of the plates. A white precipitate forms over a 1 to 2 h period leaving clearing zones of increasing intensity at the areas where increasing amounts of heparinase are added or where a bacterial colony is producing heparinase. For example, clearing zones were formed around *F. heparinum* colonies grown on LB agar plates containing 1.0 g heparin/l but not around *E. coli* JM83 grown on the same plates.

Detection of a constitutive producing strain of *F. heparinum* requires growth of the organism on medium without heparin. An assay was developed where *F. heparinum* are grown in minimal medium containing 1 mM $MgSO_4$ (repressing conditions) and plated out onto two minimal medium agar plates one of which is supplemented with 1.0 g/l heparin (inducing conditions). The plates are incubated at 30° C. for 36 h and the colonies transferred to nitrocellulose (NC) paper. *F. heparinum* colonies adhere to the NC paper and are lysed by exposure to chloroform vapors for 20 min. The NC paper is then overlayed onto heparinase assay plates (described above) and incubated at 37° C. for 1 h. The NC papers are discarded and the plates developed with 2% protamine sulfate. Clear zones appear on the plate corresponding to the cells grown under inducing conditions (heparin supplemented plate) while no zones can be detected on the plate corresponding to the cells grown under sulfate repressing conditons.

The plate assay is sufficient for detecting heparinase activity and does not require the presence of other heparin catabolic enzymes. This feature represents an improvement over previously reported methods and may therefore prove useful in screening *E. coli* expression gene banks for the cloned heparinase gene. Additionally the ability to differentiate *F. heparinum* grown under repressed and induced conditions, using NC paper, increases the usefulness of this technique in identifying constitutive mutants.

The heparinase assay based on the metachromatic shift of Azure A from blue to red in the presence of heparin was used in the development of a microculture assay to identify cells producing heparinase, particularly cells which normally do not produce heparinase such as *E. coli* which have been genetically engineered. Previous attempts to use Azure A in microculture assays were stymied by background effects, presumably due to a media component, rendering color differences in samples with or without heparin undetectable. Sodium chloride was identified as a component responsible for this background effect by adding B-broth containing 0.0 g/l heparin and varying amount of NaCl to the wells of 96-well microculture plates, then adding an equal volume of 0.04 g Azure A/l to each well and measuring the absorbance at 605 nm measured with a Titertek Multiscan plate reader. Keeping the concentration of NaCl below one g/l sufficiently reduces background effects.

The assay is as follows: modified B-broth containing bacto tryptone, 10 g/l; NaCl, 1.0 g/l; heparin 0.02 g/l; and supplemented with methionine, proline, histidine and thiamine is filter sterilized and added to microculture wells (150 µl/well). Entire rows of wells are either left uninoculated, inoculated with *E. coli* JM83 or inoculated with *F. heparinum*. One row contains modified B-broth without heparin. The plate is incubated at 30° C. for 36 h and subsequently frozen and thawed. The thawed plate is incubated at 37° C. for 3 h prior to the addition of 150 µl 0.04 mg Azure A/ml to each well and measuring the absorbance at 605 nm. Furthermore, the difference in color among the different sets of wells: uninoculated, *E.* coli JM83 cultures and *F. heparinum* cultures is detectable by simple visual observation.

SCREENING OF EXPRESSION LIBRARY FOR HEPARINASE GENES

A *F. heparinum* chromosomal gene bank was constructed in *E. coli* using the plasmid expression vector pUC18. *F. heparinum* chromosomal DNA was treated with light sonication prior to the addition of BamHI linkers and ligation into the dephosphorylated BamHI site of pUC18. 50,000 independent transformants were isolated having an average chromosomal DNA insert size of 6 kbp. The use of sonicated DNA in this construction enhances the randomness of generated fragments over those obtained by restriction enzyme digestion which cleave at specific sites, potentially located within the structural gene. This pUC18 gene bank is therefore more appropriate for use with screening techniques which rely on the expression of active protein for detection. Both assay techniques described above are being used to screen candidates from this gene bank.

The difficulties encountered in obtaining sufficiently pure preparations of heparinase could be resolved by expression of the heparinase gene in an organism such as *E. coli*. *E. coli* would provide an environment for biosynthesis, free of the contaminating background enzymes; sulfatases, glycuronidase, etc. which are present in *F. heparinum*, greatly simplifying purification processes for catalytic grade heparinase, required for blood deheparinization. Additionally one could expect an increase in product titers in a recombinant system over those displayed by *F. heparinum* fermentations. Improvement in the overall production process is necessary for the economic feasibility of an industrial scale production process. A rudimentary analysis suggests that the economic breakeven point is at a production level of $1 \times 10^6$ U pure enzyme/liter fermentation broth. Using the method of the present invention, $2 \times 10^4$ U pure enzyme/ liter can be obtained from *F. heparinum* fermentations, assuming a 20% yield.

The present invention has been described with reference to specific embodiments. Variations and modifications of these methods will be obvious to those skilled in the art from the foregoing detailed description of the invention. Such modifications and variations are intended to come within the scope of the appended claims.

We claim:

1. A composition comprising a substantially purified heparinase isolated from *Flavobacterium heparinum* bacteria by
   a) disrupting the envelope without releasing a significant amount of cytoplasmic proteins of the bacteria in an osmotically stabilized medium;
   b) releasing the non-heparinase proteins from the periplasmic space by (i) first washing the bacteria with a buffer having an ionic strength equivalent to 10 mM phosphate and adjusted to a pH between 6.0 and 8.6; and
   c) releasing the heparinase by (ii) washing the bacteria of step (i) with a buffered salt solution having an ionic strength equivalent to 0.15M sodium chloride and adjusted to a pH between 6.0 and 8.6,
   wherein the heparinase has a molecular weight between 65,000 to 75,000 by gel chromatography and a molecular weight of 70,000 by polyacrylamide gel electrophoresis in the presence of sodium disulfate under reducing or non-reducing conditions and the composition is essentially free of a heparinase having a molecular weight of 43,000 daltons by SDS-polyacrylamide gel electrophoresis.

2. The composition of claim 1 wherein the osmotically stabilized medium contains 20% sucrose.

3. The composition of claim 1, wherein the first washing solution is 10 mM phosphate adjusted to a pH of between 7.0 to 7.5 and the second washing solution is a phosphate buffer containing 0.15M sodium chloride and adjusted to a pH between 7.0 and 7.5.

4. The composition of claim 1 wherein the heparinase released into the second washing solution is further purified by cation exchange chromatography.

5. A method for isolating heparinase from *Flavobacterium heparinum* comprising:
   a) disrupting the envelope of the bacteria without releasing a significant amount of cytoplasmic proteins of the bacteria in an osmotically stabilized medium;
   b) releasing non-heparinase proteins from the periplasmic space by
      (i) first washing the bacteria with a buffered salt solution having an ionic strength equivalent to 10 mM phosphate and adjusted to a pH between 6.0 and 8.6; and
   c) releasing the heparinase by
      (ii) then washing the bacteria of step (i) with a buffered salt solution having an ionic strength equivalent to 0.15M sodium chloride and adjusted to a pH between 6.0 and 8.6.

6. The method of claim 5 wherein the osmotically stabilized medium is a 20% sucrose solution.

7. The method of claim 5 wherein the first washing solution is 10 mM phosphate adjusted to a pH of between 7.0 to 7.5 and the second washing solution is a phosphate buffer containing 0.15M sodium chloride adjusted to a pH between 7.0 and 7.5.

8. The method of claim 2 wherein the high ionic strength solution is a phosphate buffer containing 0.15M sodium chloride at a pH between 6.0 and 8.6.

9. The method of claim 5 wherein the bacteria are disrupted by addition of a compound selected from the group consisting of ethylenediaminetetraacetic acid, lysozyme, toluene, and chloroform.

10. The method of claim 5 wherein the bacteria are disrupted by freezing and thawing the bacteria cells.

11. The method of claim 5 further comprising fractionating the heparinase by cation exchange chromatography.

12. The method of claim 11 further comprising fractionating the heparinase by gel filtration.

13. The method of claim 11 further comprising fractionating the heparinase by polyacrylamide gel electrophoresis.

* * * * *